US009043722B1

(12) United States Patent
Holt (10) Patent No.: US 9,043,722 B1
(45) Date of Patent: May 26, 2015

(54) USER INTERFACES FOR DISPLAYING RELATIONSHIPS BETWEEN CELLS IN A GRID

(71) Applicant: SURFWAX, INC., Menlo Park, CA (US)

(72) Inventor: Thomas D. Holt, Atherton, CA (US)

(73) Assignee: SURFWAX, INC., Menlo Park, CA (US)

( * ) Notice: Subject to any disclaimer, the term of this patent is extended or adjusted under 35 U.S.C. 154(b) by 0 days.

(21) Appl. No.: 13/739,792

(22) Filed: Jan. 11, 2013

Related U.S. Application Data (60) Provisional application No. 61/661,633, filed on Jun. 19, 2012.

(51) Int. Cl.
*G06F 17/24* (2006.01)
*G06F 3/0484* (2013.01)
*G06F 17/30* (2006.01)

(52) U.S. Cl.
CPC .......... *G06F 17/241* (2013.01); *G06F 3/04842* (2013.01); *G06F 17/30604* (2013.01); *G05B 2219/31477* (2013.01)

(58) Field of Classification Search
CPC ............... G06F 17/246; G06F 17/245; G06F 17/30011; G06F 17/30572; G06F 17/30244; G06F 3/048; G06F 3/0482; G06F 3/0481; G06F 3/04815; G06F 2203/04804; G06F 2203/04805; G06F 2203/04806; G06F 3/04842; G06F 17/241; G06F 17/30601; G05B 2219/31477; G05B 2219/35079; G05B 2219/31485; G05B 2219/32175; G05B 2219/33134; G05B 2219/35023; G05B 2219/35155; G05B 2219/36305; G05B 2219/36306; G05B 2219/37508; G05B 2219/41206; G05B 2219/42149; G05B 23/024; G05B 23/0254; G06K 2009/62; G06K 9/00536; G06K 9/62; H04L 67/1065; H04L 67/10; H04L 45/64; G06T 11/00; G06T 19/00; G09G 5/14; G09G 5/377; H04M 1/27455; H04N 5/272; H04N 7/014
See application file for complete search history.

(56) References Cited

U.S. PATENT DOCUMENTS

| | | | |
|---|---|---|---|
| 4,790,028 A | 12/1988 | Ramage | |
| 5,075,673 A | 12/1991 | Yanker | |
| 5,215,396 A | 6/1993 | Rogers | |
| 5,416,895 A * | 5/1995 | Anderson et al. | ............. 715/209 |
| 5,485,174 A | 1/1996 | Henshaw et al. | |

(Continued)

FOREIGN PATENT DOCUMENTS

WO    WO 2012/112356    8/2012

OTHER PUBLICATIONS

"A User-Centred Approach to Functions in Excel" by Simon Peyton Jones et al.*

(Continued)

*Primary Examiner* — Boris Pesin
*Assistant Examiner* — Paul Thatcher
(74) *Attorney, Agent, or Firm* — Maschoff Brennan (57) ABSTRACT

User interfaces for displaying relationships between cells in a grid. In one example embodiment, a user interface includes a grid including rows and columns and a plurality of cells each having a specific position in the grid. A first one of the cells is related to a second one of the cells. The grid is configured to display, upon selection of the first cell or second cell, a visual representation of the relationship between the first cell and the second cell.

20 Claims, 6 Drawing Sheets

(56) References Cited

U.S. PATENT DOCUMENTS

| | | | |
|---|---|---|---|
| 5,581,670 A | 12/1996 | Bier et al. |
| 5,617,114 A | 4/1997 | Bier et al. |
| 5,689,717 A | 11/1997 | Pritt |
| 5,732,230 A | 3/1998 | Cullen et al. |
| 5,798,752 A | 8/1998 | Buxton et al. |
| 5,920,841 A | 7/1999 | Schottmuller et al. |
| 5,943,679 A | 8/1999 | Niles et al. |
| 5,978,747 A | 11/1999 | Craport et al. |
| 6,016,144 A | 1/2000 | Blonstein et al. |
| 6,118,427 A | 9/2000 | Buxton et al. |
| 6,121,966 A | 9/2000 | Teodosio et al. |
| 6,185,582 B1 * | 2/2001 | Zellweger et al. | 715/212 |
| 6,278,660 B1 | 8/2001 | Tognazzini |
| 6,320,495 B1 | 11/2001 | Sporgis |
| 6,397,143 B1 | 5/2002 | Peschke |
| 6,407,749 B1 | 6/2002 | Duke |
| 6,421,063 B1 | 7/2002 | Morrison |
| 6,424,355 B2 | 7/2002 | Watanabe et al. |
| 6,476,831 B1 | 11/2002 | Wirth et al. |
| 6,509,915 B2 | 1/2003 | Berman et al. |
| 6,642,936 B1 | 11/2003 | Engholm et al. |
| 6,643,656 B2 | 11/2003 | Peterson |
| 6,657,644 B1 | 12/2003 | Plow et al. |
| 6,792,776 B2 | 9/2004 | Davis et al. |
| 6,915,409 B1 | 7/2005 | Peterson |
| 7,051,289 B1 | 5/2006 | Yoshida |
| 7,051,291 B2 | 5/2006 | Sciammarella et al. |
| 7,068,290 B2 | 6/2006 | Bennett et al. |
| 7,076,409 B2 | 7/2006 | Agrawala et al. |
| 7,106,220 B2 | 9/2006 | Gourgey et al. |
| 7,107,532 B1 | 9/2006 | Billmaier et al. |
| 7,133,862 B2 * | 11/2006 | Hubert et al. | 1/1 |
| 7,197,718 B1 | 3/2007 | Westerman et al. |
| 7,269,794 B2 | 9/2007 | Martinez et al. |
| 7,274,377 B2 | 9/2007 | Ivashin et al. |
| 7,274,378 B2 | 9/2007 | McAvoy et al. |
| 7,320,031 B2 | 1/2008 | Konig et al. |
| 7,340,418 B2 | 3/2008 | Caine |
| 7,405,739 B2 | 7/2008 | Gannon |
| 7,437,279 B2 | 10/2008 | Agrawala et al. |
| 7,496,484 B2 | 2/2009 | Agrawala et al. |
| 7,500,197 B2 | 3/2009 | Whitmarsh et al. |
| 7,559,036 B1 | 7/2009 | Buck |
| 7,587,276 B2 | 9/2009 | Gold et al. |
| 7,770,130 B1 | 8/2010 | Suzuki |
| 7,844,395 B2 | 11/2010 | Aoyama |
| 7,990,394 B2 | 8/2011 | Vincent et al. |
| 7,995,078 B2 | 8/2011 | Baar |
| 8,037,422 B1 | 10/2011 | Buck |
| 8,115,764 B2 | 2/2012 | Kameda et al. |
| 8,120,624 B2 | 2/2012 | Jetha et al. |
| 8,122,341 B1 | 2/2012 | Dayan et al. |
| 8,151,215 B2 | 4/2012 | Baurmann et al. |
| 8,180,690 B2 | 5/2012 | Mayle et al. |
| 8,209,372 B2 | 6/2012 | Abdo et al. |
| 8,219,927 B2 | 7/2012 | Gatlin et al. |
| 8,225,225 B2 | 7/2012 | Jetha et al. |
| 8,245,255 B2 | 8/2012 | Schlarb |
| 8,255,238 B2 | 8/2012 | Powell et al. |
| 8,265,864 B1 | 9/2012 | Kaufman et al. |
| 8,269,767 B2 | 9/2012 | Glueck et al. |
| 8,270,769 B2 | 9/2012 | Judelson |
| 8,294,710 B2 | 10/2012 | Kinnan et al. |
| 8,314,789 B2 | 11/2012 | Fitzmaurice et al. |
| 8,321,804 B2 | 11/2012 | Castelli et al. |
| 8,321,806 B2 | 11/2012 | Agrusa et al. |
| 8,339,417 B2 | 12/2012 | Stroila et al. |
| 8,359,545 B2 | 1/2013 | Pixley et al. |
| 8,381,121 B2 | 2/2013 | Gupta et al. |
| 8,384,726 B1 | 2/2013 | Grabowski et al. |
| 8,386,920 B2 | 2/2013 | Cox et al. |
| 8,397,180 B2 | 3/2013 | Duhig |
| 8,539,339 B2 | 9/2013 | Lloyd et al. |
| 8,582,849 B2 | 11/2013 | Eichhorn et al. |
| 2001/0018365 A1 | 8/2001 | Orui et al. |
| 2001/0034588 A1 | 10/2001 | Agrawals et al. |
| 2001/0035880 A1 | 11/2001 | Musatov et al. |
| 2002/0044144 A1 | 4/2002 | Inoue |
| 2002/0163547 A1 | 11/2002 | Abramson et al. |
| 2003/0025734 A1 * | 2/2003 | Boose et al. | 345/765 |
| 2003/0033329 A1 * | 2/2003 | Bergman et al. | 707/503 |
| 2003/0052896 A1 | 3/2003 | Higgins et al. |
| 2003/0144047 A1 | 7/2003 | Sprogis et al. |
| 2004/0056904 A1 * | 3/2004 | Jaeger | 345/853 |
| 2004/0090472 A1 | 5/2004 | Risch et al. |
| 2004/0212615 A1 * | 10/2004 | Uthe | 345/440 |
| 2004/0239681 A1 | 12/2004 | Robotham et al. |
| 2004/0263512 A1 | 12/2004 | Santodomingo et al. |
| 2004/0267700 A1 * | 12/2004 | Dumais et al. | 707/2 |
| 2004/0268299 A1 | 12/2004 | Lei et al. |
| 2005/0071349 A1 | 3/2005 | Jordan et al. |
| 2005/0076361 A1 | 4/2005 | Choi et al. |
| 2005/0102634 A1 | 5/2005 | Sloo |
| 2005/0125739 A1 | 6/2005 | Thompson et al. |
| 2005/0132305 A1 | 6/2005 | Guichard et al. |
| 2005/0138570 A1 | 6/2005 | Good et al. |
| 2005/0182604 A1 | 8/2005 | Agrawala et al. |
| 2005/0210403 A1 | 9/2005 | Satanek |
| 2005/0257166 A1 | 11/2005 | Tu |
| 2006/0048073 A1 | 3/2006 | Jarrett et al. |
| 2006/0059063 A1 | 3/2006 | LaComb et al. |
| 2006/0080594 A1 * | 4/2006 | Chavoustie et al. | 715/503 |
| 2006/0247850 A1 | 11/2006 | Cera et al. |
| 2006/0253795 A1 | 11/2006 | Titov et al. |
| 2006/0287815 A1 | 12/2006 | Gluck |
| 2007/0072629 A1 | 3/2007 | Bae |
| 2007/0130515 A1 | 6/2007 | Maas |
| 2007/0136286 A1 | 6/2007 | Webster et al. |
| 2007/0136406 A1 * | 6/2007 | Softky | 708/200 |
| 2007/0179776 A1 * | 8/2007 | Segond et al. | 704/9 |
| 2007/0198476 A1 | 8/2007 | Farago et al. |
| 2007/0245247 A1 | 10/2007 | Neely et al. |
| 2008/0002911 A1 | 1/2008 | Eisen et al. |
| 2008/0052372 A1 | 2/2008 | Weber et al. |
| 2008/0103695 A1 | 5/2008 | Whiting |
| 2008/0155474 A1 | 6/2008 | Duhig |
| 2008/0155475 A1 | 6/2008 | Duhig |
| 2008/0208631 A1 | 8/2008 | Morita et al. |
| 2008/0208880 A1 * | 8/2008 | Dong et al. | 707/101 |
| 2008/0291205 A1 | 11/2008 | Rasmussen et al. |
| 2008/0292213 A1 | 11/2008 | Chau |
| 2009/0013273 A1 | 1/2009 | Fuchs et al. |
| 2009/0030556 A1 | 1/2009 | Castelli et al. |
| 2009/0083676 A1 * | 3/2009 | Flanagan et al. | 715/853 |
| 2009/0100373 A1 | 4/2009 | Pixley et al. |
| 2009/0158185 A1 | 6/2009 | Lacevic et al. |
| 2009/0160873 A1 | 6/2009 | Kew et al. |
| 2009/0183095 A1 | 7/2009 | Deitsch et al. |
| 2009/0199142 A1 | 8/2009 | Arunachalam et al. |
| 2009/0204920 A1 | 8/2009 | Beverley et al. |
| 2009/0228841 A1 * | 9/2009 | Hildreth | 715/863 |
| 2010/0011316 A1 | 1/2010 | Sar et al. |
| 2010/0020093 A1 | 1/2010 | Stroila et al. |
| 2010/0031152 A1 | 2/2010 | Villaron et al. |
| 2010/0045702 A1 | 2/2010 | Doyle et al. |
| 2010/0058240 A1 | 3/2010 | Bull et al. |
| 2010/0115462 A1 | 5/2010 | Spencer et al. |
| 2010/0146434 A1 | 6/2010 | Blinnikka et al. |
| 2010/0194744 A1 | 8/2010 | Glueck et al. |
| 2010/0198653 A1 | 8/2010 | Bromenshenkel et al. |
| 2010/0199213 A1 | 8/2010 | Suzuki |
| 2010/0205520 A1 | 8/2010 | Parish et al. |
| 2011/0047504 A1 | 2/2011 | Wienands et al. |
| 2011/0113334 A1 | 5/2011 | Joy et al. |
| 2011/0126148 A1 | 5/2011 | Krishnaraj et al. |
| 2011/0126156 A1 | 5/2011 | Krishnaraj et al. |
| 2011/0131597 A1 | 6/2011 | Cera et al. |
| 2011/0214085 A1 | 9/2011 | Vanbree |
| 2011/0252299 A1 | 10/2011 | Lloyd et al. |
| 2011/0307772 A1 | 12/2011 | Lloyd et al. |
| 2012/0005623 A1 | 1/2012 | Ishak et al. |
| 2012/0036455 A1 | 2/2012 | Holt et al. |
| 2012/0038662 A1 | 2/2012 | Dicklin et al. |
| 2012/0054653 A1 | 3/2012 | Grossman et al. |

(56) References Cited

U.S. PATENT DOCUMENTS

| | | |
|---|---|---|
| 2012/0066638 A1 | 3/2012 | Ohri |
| 2012/0089914 A1 | 4/2012 | Holt et al. |
| 2012/0110621 A1 | 5/2012 | Gossweiler, III |
| 2012/0117452 A1 | 5/2012 | Lloyd et al. |
| 2012/0151406 A1 | 6/2012 | Oberstein |
| 2012/0151408 A1 | 6/2012 | Groth et al. |
| 2012/0188280 A1 | 7/2012 | Charlebois et al. |
| 2013/0057579 A1 | 3/2013 | Castelli et al. |
| 2013/0120460 A1 | 5/2013 | Adams et al. |

OTHER PUBLICATIONS

"Tools for spreadsheet auditing" by Davis.*
"Contour line", From Wiki.GIS.com, Revision as of 21:34, Jul. 8, 2009, by Justicelovespeace, downloaded from http://wiki.gis.com/wiki/index.php?title=Contour_line&oldid=169596 on May 1, 2013.*
"hExcel—A Hexagonal Spreadsheet", by secretGeek, archived Jul. 9, 2009 by Internet WaybackMachine, downloaded May 2, 2013.*
"Excel VLOOKUP" by Ted French downloaded from Internet Wayback Machine on Jan. 24, 2014 archived between Jan. 9, 2007 and Mar. 3, 2007 from http://web.archive.org/web/20070109071521/http://spreadsheets.about.com/od/excelfunctions/ss/vlookup.htm.*
A Negotiation Architecture for Fluid Documents Bay-Wei Chang et al.*
"Microsoft Excel 2007: The Average Function in Excel 2007" by Free Computer Tutorials downloaded Jan. 27, 2014 from https://web.archive.org/web/20080111133824/http://www.homeandlearn.co.uk/excel2007/excel2007s5p1.html archived Jan. 11, 2008.*
"3D Interactive Visualization for Inter-Cell Dependencies of Spreadsheets" by Hidekazu Shiozawa et al, IEEE Symposium on Information Visualization, 1999. (Info Vis '99) Proceedings. 1999.*
"A User-Centred Approach to Functions in Excel", Simon Peyton et al.*
"Fluid Visualization of Spreadsheet Structures" by Takeo Igarashi et al.*
"Visualizing Locations of Off-Screen Objects on Mobile Devices: A Comparative Evaluation of Three Approaches" by Stefano Burigat et al MobileHCI '06, Sep. 12-15, 2006, Helsinki, Finland. Copyright 2006 ACM.*
"EXChecker v2.4: EXChecker Help" published 2005 by Spreadsheet auditing Ltd.*
U.S. Appl. No. 13/739,819, filed Jan. 11, 2013 titled "User Interfaces for Summarizing Statuses of Cells in a Grid".
U.S. Appl. No. 13/739,834, filed Jan. 11, 2013 titled "User Interfaces Employing Background Images, Branching Cells, and Hidden Cells for Navigating Cells in a Grid".
U.S. Appl. No. 13/739,880, filed Jan. 11, 2013 titled "User Interfaces for Interrupted Grid Navigation, Multi-Input Scrolling, and Displaying Spanner Cells".
International Search Report mailed Sep. 27, 2012 in related PCT Patent Application No. PCT/US2012/024253.
U.S. Appl. No. 13/739,819, filed Aug. 7, 2013, Office Action.
U.S. Appl. No. 13/739,819, filed Jan. 14, 2014, Office Action.
U.S. Appl. No. 13/739,834, filed May 22, 2013, Office Action.
U.S. Appl. No. 13/739,834, filed Oct. 21, 2013, Office Action.
U.S. Appl. No. 13/739,880, filed Jun. 20, 2013, Office Action.
U.S. Appl. No. 13/739,880, filed Jul. 25, 2013, Office Action.
U.S. Appl. No. 13/739,880, filed Feb. 27, 2014, Office Action.

* cited by examiner

USER INTERFACES FOR DISPLAYING RELATIONSHIPS BETWEEN CELLS IN A GRID

CROSS-REFERENCE TO A RELATED APPLICATION

This application claims priority to and the benefit of U.S. Provisional Patent Application Ser. No. 61/661,633, titled "USER INTERFACES FOR NAVIGATING RELATIONAL STRUCTURED CONTENT AND SUMMATIVE DISPLAYS," filed on Jun. 19, 2012, which is incorporated herein by reference in its entirety.

BACKGROUND

Grid-based user interfaces often store content in rows and columns of cells. In general, cells in a row are related in some manner and/or cells in a column are also related in some manner. However, beyond simple relationships that are manifest by the row and/or column positioning of a cell, cells may have other relationships to cells that do not share the same row and/or the same column. Such relationships may not be perfectly linear as implied by the X-Y structure of a grid. Unfortunately, current grid-based user interfaces are not capable of establishing and displaying relationships between individual cells in a grid beyond basic row and/or column positioning of cells.

BRIEF SUMMARY OF SOME EXAMPLE EMBODIMENTS

In general, example embodiments of the invention relate to user interfaces for displaying relationships between cells in a grid. At least some of the example user interfaces disclosed herein enable relationships between individual cells in a grid to be established and displayed, upon selection of one of the related cells, in the user interface. These embodiments enable nonlinear relationships to be displayed outside of the normal parameters of the contiguous X-Y structure of the grid.

In one example embodiment, a user interface includes a grid including rows and columns and a plurality of cells each having a specific position in the grid. A first one of the cells is related to a second one of the cells. The grid is configured to display, upon selection of the first cell or second cell, a visual representation of the relationship between the first cell and the second cell.

In another example embodiment, a user interface includes a grid including rows and columns, a viewport that displays only a portion of the grid, and a plurality of cells each having a specific position in the grid. A first one of the cells is related to a second one of the cells that is positioned in a different row and/or a different column from the first cell. The viewport is configured to display, upon selection of the first or second cell, a visual representation of the relationship in the viewport between the first cell and the second cell.

In yet another example embodiment, a user interface includes a grid including rows and columns, a viewport that displays only a portion of the grid, and a plurality of cells each having a specific position in the grid. A first one of the cells is related to a second one of the cells that is positioned in a different row and/or a different column from the first cell such that the first cell and the second cell are not capable of being displayed in the viewport at the same time. The viewport is configured to display, upon selection of the first cell displayed in the viewport, a visual representation in the viewport of the relationship between the first cell and the second cell.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features will be set forth in the description which follows or may be learned by the practice of the teachings herein. Features of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify certain aspects of the present invention, a more particular description of the invention will be rendered by reference to example embodiments thereof which are disclosed in the appended drawings. It is to be understood that the drawings are diagrammatic and schematic representations of such example embodiments, and are not limiting of the present invention, nor are they necessarily drawn to scale. Aspects of the invention will be described and explained with additional specificity and detail through the use of the accompanying drawings in which:

FIG. 2 illustrates the example user interface of FIG. 1 with the user interface displaying a visual representation of relationships between cells using lines connecting the cells;

DETAILED DESCRIPTION OF SOME EXAMPLE EMBODIMENTS

Example embodiments of the present invention relate to user interfaces for displaying relationships between cells in a grid. At least some of the example user interfaces disclosed herein enable relationships between individual cells in a grid to be established and displayed, upon selection of one of the related cells, in the user interface. These embodiments enable nonlinear relationships to be displayed outside of the normal parameters of the contiguous X-Y structure of the grid.

As used herein, the term "grid" is not limited to a grid made up of rectangular cells organized into X-Y rows and columns. Therefore, although the grids of the example user interfaces disclosed herein are generally grids made up of rectangular cells organized into X-Y rows and columns, it is understood that the term "grid" can also encompass a grid with non-rectangular cells, such as a spherical grid, and/or a grid that does not have linear vertical and horizontal X-Y rows and columns, such as diagonal or curved rows and columns.

Figure 1:
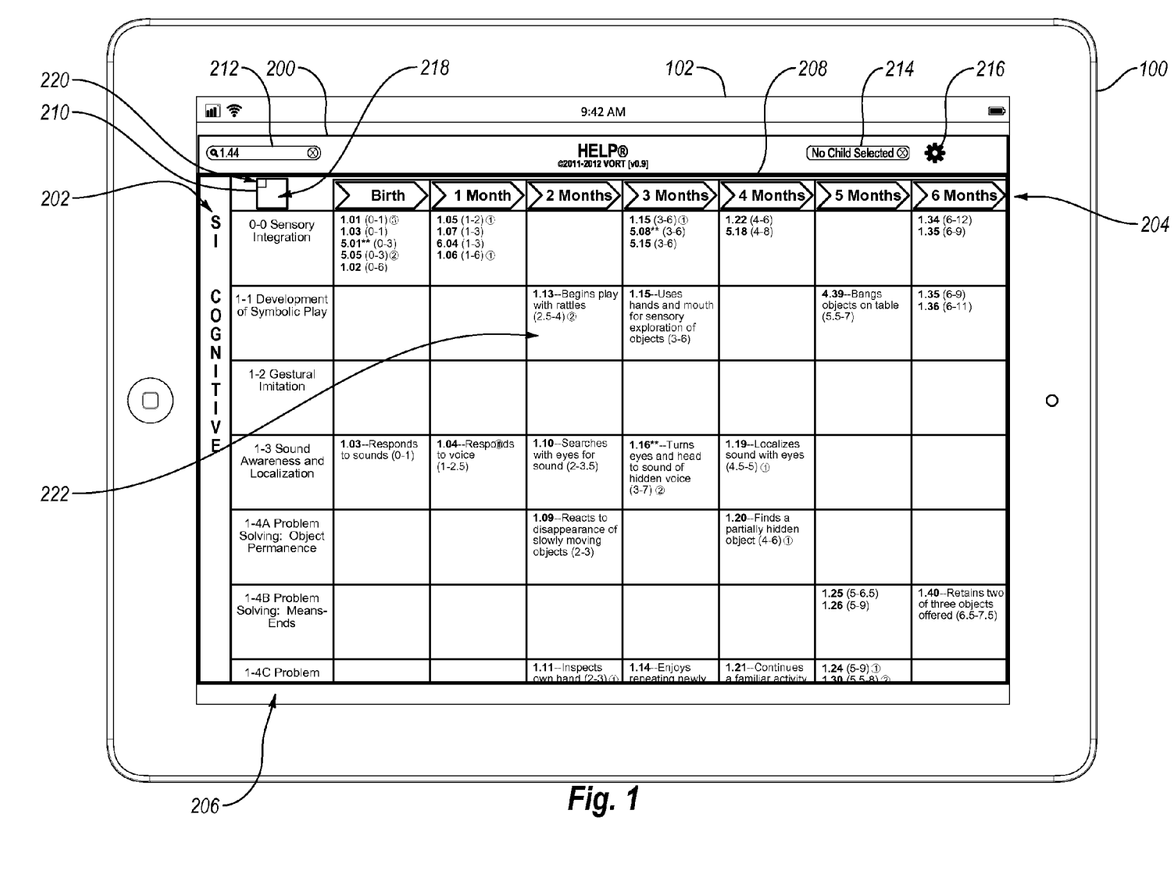
FIG. 1 illustrates an example tablet computer environment in which an example user interface having a grid of cells is displayed.

FIG. 1 illustrates an example tablet computer environment in which an example user interface having a grid of cells is displayed. In particular, FIG. 1 discloses a tablet computer 100 having a touch display area 102. The touch display area 102 is employed in FIG. 1 to display an example user interface 200. The user interface 200 includes a grid 202. The grid 202 has rows and columns of cells, with each cell having a specific position in the grid. Each cell is configured to contain content, such as the structured content disclosed in U.S. patent application Ser. No. 13/271,882, which was filed on Oct. 12, 2011, and which is incorporated herein by reference in its entirety. Some of the cells in the grid 202 may be cluster cells. A cluster cell is a cell which itself may contain two or more separate additional cells. The grid 202 includes a header row 204 and a header column 206.

The user interface 200 also includes a viewport 208, a viewtracker 210, a search box 212, a target box 214, and a user options selector 216.

Since the grid 202 is too large to be displayed all at once, the viewport 208 displays only a portion of the grid 202. The user interface 200 enables a user to reposition the grid 202 within the viewport 208 to allow the user to navigate to any portion of the grid 202. This repositioning may be accomplished, for example, by dragging the grid using a mouse pointer on a non-touch display or using a finger on a touch display.

The viewtracker 210 includes a grid representation 218 of the grid 202 and a viewport representation 220 of the viewport 208. The viewport representation 220 is positioned within the grid representation 218 and overlays the grid representation 218. The viewport representation 220 visually conveys both the proportion of the grid 202 currently displayed in the viewport 208 as well as the position within the grid 202 of the portion of the grid 202 displayed in the viewport 208, thereby helping the user visualize where the user is in terms of either additional or total content to be viewed or progress along the progression of the grid 202. During scrolling within the viewport 208, the viewport representation 220 may also convey the rate of travel through the grid 202.

The search box 212 allows a user to search for a specific cell or a specific cell content within the grid 202. The target box 214 displays the target of the grid. The target of the grid 202 may be, for example, an individual, a group of individuals, an animal, a computer program, a project, a company, a car model, a series of paintings, or anything to which a range or value or rating or score can be determined or assigned, for which a sense of status change or progress can be represented or tracked. In FIG. 1, the target box 214 displays the name of a target individual associated with the cell contents or cell statuses of the cells currently displayed in the grid 202. The target individual may be different from the user of the user interface 200. For example, the target individual may be a child and the user of the user interface 200 may be the child's parent, teacher, or physician. The user may access the user interface 200 to track the developmental progress of the child in each of the developmental areas covered by the content contained in each cell. Alternatively, for example, the user may be a car salesman, with the target being a specific make of car selectable under the user options selector 216 of different makes of car, with the status representing consumer ratings on the features of different models of that make of car. The user options selector 216 may be selected by the user in order to access various option menus related to the user interface 200.

Additional details about cluster cells, header rows, and header columns, viewports, viewtrackers, and search boxes are disclosed in U.S. patent application Ser. No. 13/271,882.

Each of the cells disclosed in the grid 202 of FIG. 1 may be related to one or more of the other cells in the grid 202. As used herein, the phrase "a first cell and a second cell are related cells" or "a first cell is related to a second cell" refers to the content of the first cell of a grid and the content of the second cell of the grid being related. As noted previously, these relationships may not be perfectly linear as implied by the X-Y structure of the grid 202. Further, it is noted that a single cell may be related to multiple other cells (i.e., one-to-many relationships), and multiple cells may be related to multiple other cells (i.e., many-to-many relationships). Therefore, although many of the example relationships disclosed herein relate a first cell to a single cell, it is understood that various one-to-many and many-to-many combinations of relationships are also possible. It is further noted that although the relationships disclosed between cells herein are generally direct relationships (where one cell is directly related to another cell), various indirect relationships may also be defined and exist between cells in the grid 202. For example, if a first cell is directly related to a second cell via a first direct relationship, and the second cell is directly related to a third cell via a second direct relationship, the first cell is indirectly related to the third cell via the first and second direct relationships.

A relationship between cells may have one or more aspects. An aspect of a relationship may include, but is not limited to, the relationship's type, degree, weight, magnitude, order, or sequence. A relationship type may be, for example, a human relationship (e.g., parent/child, sibling, child/parent, or spouse), an organizational relationship (e.g., employer/employee, investor/board, or parent corporation/subsidiary), a logical relationship (e.g., related "see also" content or prerequisite), a conceptual relationship (e.g., a broader concept in one cell and a narrower concept in another cell), or a semantic relationship (e.g., the meaning of words in one cell being semantically related to the meaning of words in another cell). Other relationship aspects are also possible, and the term "aspect" is not limited to these examples.

The relationships between cells may be established manually by a user or automatically by the user interface 200 and these relationships may be viewed as nodes along a "relational thread". For example, the user interface 200 may be configured to allow a user to specify the relationship and one or more aspects of the relationship between two or more cells. This may be accomplished using an options display (not shown) that is accessed by selecting the user options selector 216 of the user interface 200. As used herein, the term "user" includes not only an end user of the user interface 200, but any other user, such as a content author or an interface administrator. Also, the user interface 200 may be configured to allow a user to create and define custom relationships between cells by using any of various methods, for example, using a provided drawing palette provided within the user interface 200 that includes pre-defined relational data objects and drawing tools that the user may assign to cell pairs or groupings of cells. Similarly, the user interface 200 may automatically establish relationships between cells by, for example, matching cell content or tracking user interaction patterns with cells.

The user interface 200 may also be configured to display a related-cells indicator when a cell has related cells. For example, where a cell in the grid 202 has a certain number of related cells, that number may be displayed in the cell inside a circle as disclosed in FIG. 1. For example, the cell 222 includes two related cells, as indicated by the circle with the number "2" in the cell 222. Using a related-cells indicator may enable a user to quickly ascertain which cells have a related cell, and also ascertain certain aspects of those relationships such as how many such relationships exist.

It is understood that although the user interface 200 is disclosed in FIG. 1 in a tablet computer environment, the user interface 200 may instead be employed in a variety of other environments including other touch display environments as well as non-touch display environments.

FIG. 2 illustrates the example user interface 200 displaying a visual representation of relationships between cells using lines connecting the cells. In particular, FIG. 2 discloses the user interface 200 upon selection of the cell 222. The cell 222 may be selected, for example, by double clicking or double tapping on the cell 222. The cell 222 may alternatively be selected in a variety of other predetermined ways. Upon selection, the lines 224 and 226 appear connecting to the cells 228 and 230, respectively. One or more aspects of the relationship visually represented by a line may be represented by the color, weight, or style of the line. For example, the style of the line 224 is a dot-dot-dashed arrow pointing from the cell 228, which represents that the cell 228 has a "prerequisite" relationship to the cell 222. In contrast, the style of the line 226 is a dashed arrow pointing to the cell 230, which represents that the cell 230 has a "see also" relationship to the cell 222. It is understood that the relationship types of "prerequisite" and "see also" are used herein as example aspects of a relationship between cells, but other aspects of a relationship can also be represented by the color, weight, style, or other characteristics of the line. Thus, FIG. 2 illustrates that lines 224 and 226 connecting cells 222, 228, and 230 together is one form of a visual representation of the relationships between these cells.

Although lines are used in FIG. 2 as a form of a visual representation of the relationships between cells, it is understood that lines are but one form of a visual representation of the relationships between cells. Other possible forms that could instead be employed in FIG. 2 include, but are not limited to, other graphic objects, such as a series of bubbles or balloons, a simple vector arrow that is not a full line, or an animated object such as an orbiting star or symbol. Thus, the discussion of "lines" herein could also apply to any other form of graphic or symbolic representation.

Figure 3:
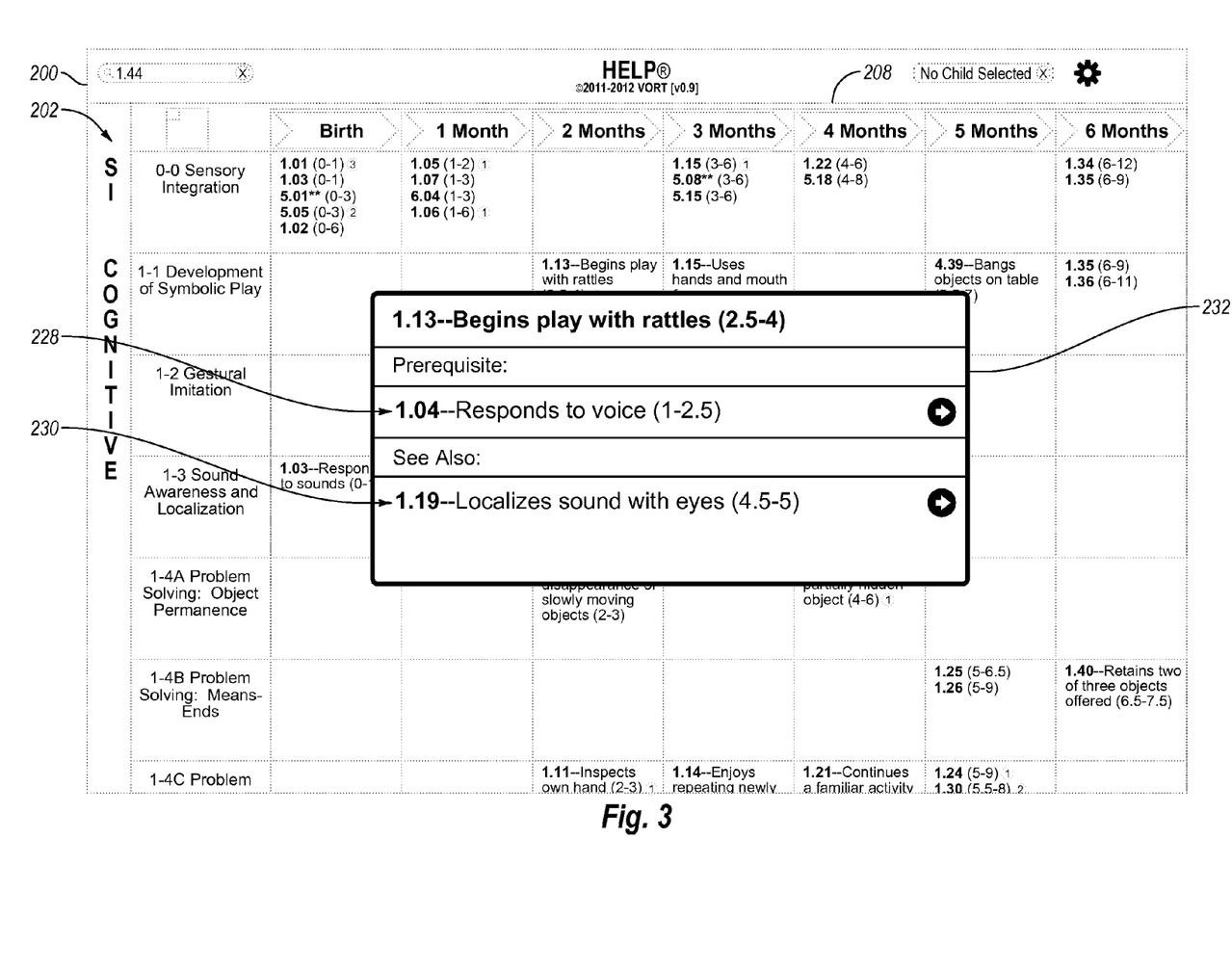
FIG. 3 illustrates the example user interface of FIG. 1 with the user interface displaying a visual representation of relationships between cells using a separate interface object that lists the relationships.

FIG. 3 illustrates the example user interface 200 displaying a visual representation of relationships between cells using a separate interface object that lists the relationships. In particular, FIG. 3 discloses the user interface 200 upon selection of the cell 222. Upon selection, a separate interface object, namely, a pop-up window 232 is displayed in the viewport 208 in front of the grid 202. The pop-up window 232 lists the "prerequisite" relationship between the cell 228 and the cell 222 and the "see also" relationship between the cell 222 and the cell 230. Thus, FIG. 3 illustrates that the pop-up window 232 that lists the relationships between the cells 222, 228, and 230 is another form of a visual representation of the relationships between these cells.

Figure 4:
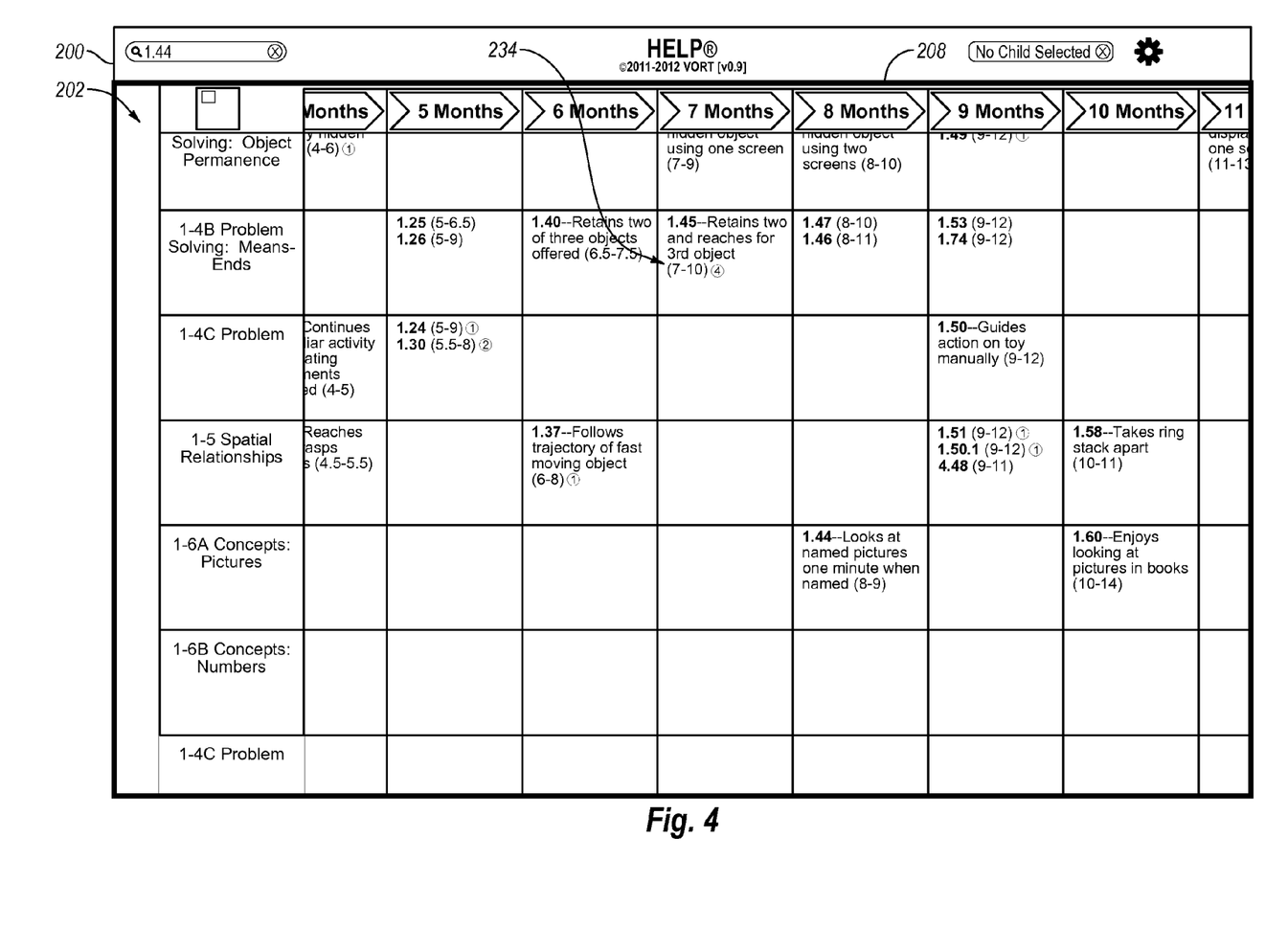
FIG. 4 illustrates the example user interface of FIG. 1 displaying a different portion of the grid.

FIG. 4 illustrates the example user interface 200 displaying a different portion of the grid 202 in the viewport 208. As disclosed in FIG. 4, the cell 234 includes four related cells, as indicated by the related-cells indicator of the circle with the number "4" in the cell 234.

Figure 5:
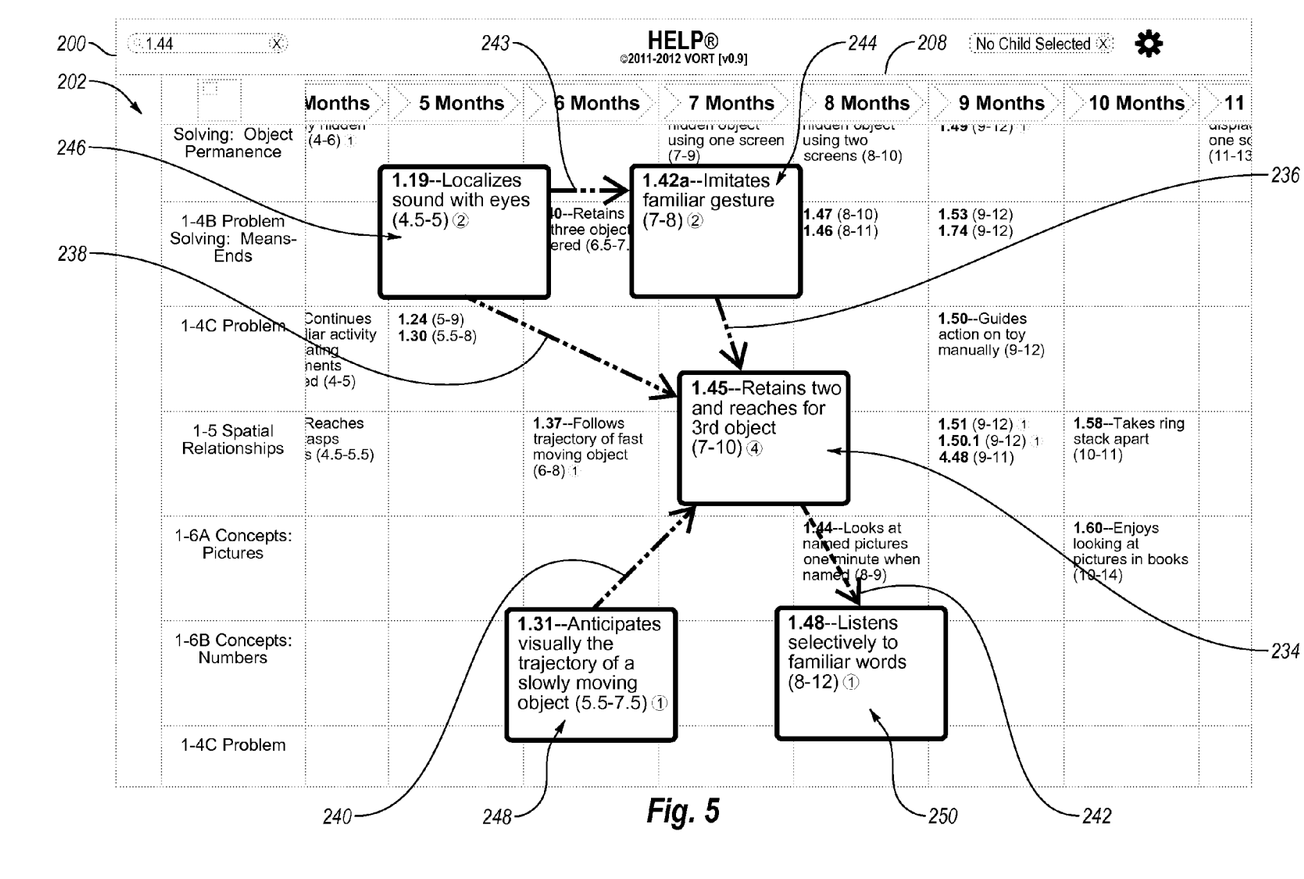
FIG. 5 discloses the example user interface of FIG. 4 with the user interface displaying a visual representation of relationships between cells using gathered cells that are gathered into the viewport and are connected to one another by lines.

FIG. 5 discloses the example user interface 200 displaying a visual representation of relationships between cells using gathered cells that are gathered into the viewport 208 and are connected to one another by lines. As used herein, the term "gathered" refers to a cell or a copy of a cell that has been repositioned out of its original position in a grid. The cell may be further modified in its size, shape, or other visual aspect of its appearance.

In particular, FIG. 5 discloses the user interface 200 upon selection of the cell 234. Upon selection, the lines 236-242 appear connecting to the cells 244-250, respectively. As noted previously, the dot-dot-dashed arrow style of the lines 236-240 represents that the cells 244-248 have "prerequisite" relationships to the cell 234. Also, the dashed arrow style of the line 242 represents the cell 250 has a "see also" relationship to the cell 234. In addition, since the cells 234 and 244-250 are not capable of being displayed in the viewport 208 due to their respective positions in the grid 202, the user interface 200 is configured to display the lines 236-242 after displaying gathered versions of the cells 234 and 244-250 that are gathered into the viewport 208. The gathered versions of the cells 234 and 244-250 may be the actual cells 234 and 244-250 having been gathered into the viewport 208, or they may be copies of the actual cells 234 and 244-250 that are gathered into the viewport 208. As disclosed in FIG. 5, the gathered versions of the cells 234 and 244-250 may be overlaid on top of the underlying grid 202. As disclosed in FIG. 5, the gathered versions of the cells 234 and 244-250 may also be enlarged, the corners may be rounded, and the borders may be thickened to emphasize the gathered versions of the cells 234 and 244-250 and deemphasize the underlying grid 202. The underlying grid 202 may be "grayed-out" or diminished in some other fashion to further emphasize the gathered versions of the cells 234 and 244-250 and further deemphasize the underlying grid 202. The gathered versions of the cells 234 and 244-250 may also be overlaid on top of the underlying grid 202 with some degree of transparency to the underlying grid 202. Thus, FIG. 5 illustrates that lines 236-242 connecting cell 234 and gathered cells 244-250 together is another form of a visual representation of the relationships between these cells.

FIG. 5 also discloses various indirect relationships between cells in the grid 202 of the user interface 200. In particular, by virtue of cell 246 being directly related to the cell 234 via the "prerequisite" relationship 238, and the cell 234 being directly related to the cell 250 via the "see also" relationship 242, the cell 246 is indirectly related to the cell 250 via these two relationships 238 and 242. Similarly, by virtue of cell 246 being directly related to the cell 234 via the "prerequisite" relationship 238, and the cell 248 being directly related to the cell 234 via the "prerequisite" relationship 240, the cell 246 is indirectly related to the cell 248 via these two relationships 238 and 240. Thus, FIG. 5 illustrates that both direct and indirect relationships can be visually represented using the lines 236, 238, 240, and 242 connecting cell 234 and gathered cells 244, 246, 248, and 250. It is understood that other forms of visually representing indirect relationships between cells can also be employed in the user interface 200.

FIG. 5 also discloses additional direct relationships between cells in the grid 202 of the user interface 200. In particular, since the cells 246 and 244 are both directly related to the cell 234, and thus are shown in the display of FIG. 5 which is presented upon selection of the cell 234, the direct "prerequisite" relationship 243 between the cell 246 and the cell 244 is also shown in the display of FIG. 5. Thus, selection of a single cell can result in the display of a web of relationships between cells that are directly related to the selected cell.

Further, in other example embodiments, the selection of a single cell can result in the display of a web of relationships between cells that are even indirectly related to the selected cell. In these example embodiments, the entire web of cell may be gathered into the viewport 208 and possibly reduced in size to allow all cells in the web to fit in the viewport 208.

Figure 6:
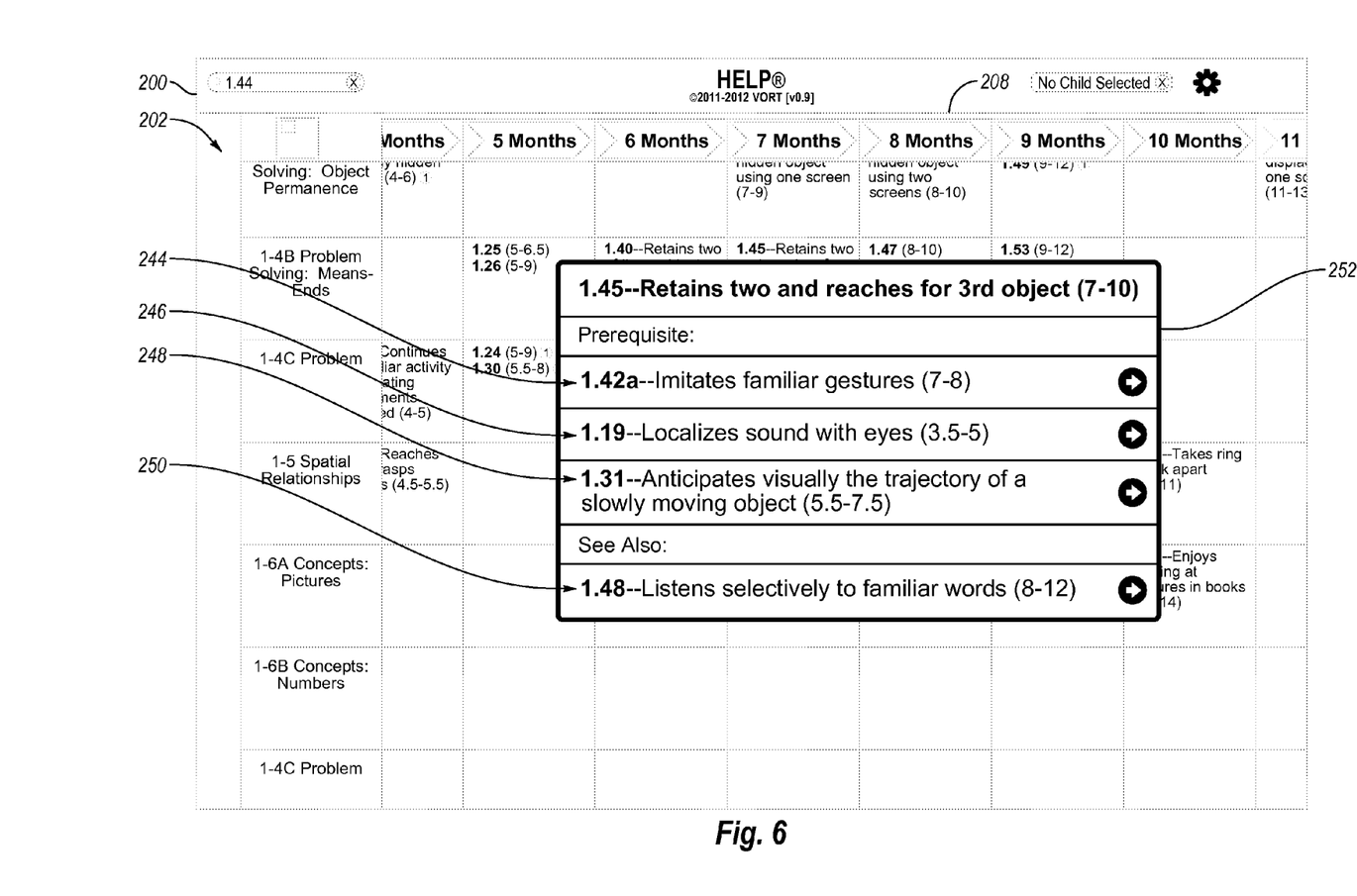
FIG. 6 discloses the example user interface of FIG. 4 with the user interface displaying a visual representation of relationships between cells using a separate interface object that lists the relationships.

FIG. 6 discloses the example user interface 200 displaying a visual representation of relationships between cells using a separate interface object that lists the relationships. In particular, FIG. 6 discloses the user interface 200 upon selection of the cell 234. Upon selection, a separate interface object, namely, a pop-up window 252 is displayed in the viewport 208 in front of the grid 202. The pop-up window 252 lists the "prerequisite" relationships between the cells 244, 246, and 248 and the cell 234 and the "see also" relationship between the cell 234 and the cell 250, similar to the pop-up window 232 disclosed in FIG. 3.

It is understood that while the lines, pop-up windows, and gathered cells with lines are disclosed herein as three example forms of a visual representation of relationships between cells, various other forms of a visual representation of relationships between cells are also possible. Therefore, the phrase "a visual representation of a relationship between cells," or variations thereof, is not limited to one of these three example forms.

The embodiments described herein may include the use of a special purpose or general purpose computer including, but not limited to, a cell phone, smartphone, smart appliance, automobile, navigation system, tablet computer, laptop computer, desktop computer, media player, and the like that is equipped with a display, including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including RAM, ROM, EEPROM, CD-ROM or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological steps, it is to be understood that the subject matter defined in the appended claims is not necessarily limited to the specific features or steps described above. Rather, the specific features and steps described above are disclosed as example forms of implementing the claims.

As used herein, the term "module" may refer to software objects or routines that execute on a computing system. The different modules described herein may be implemented as objects or processes that execute on a computing system (e.g., as separate threads). While the system and methods described herein are preferably implemented in software, implementations in hardware or a combination of software and hardware are also possible and contemplated.

All examples and conditional language recited herein are intended for pedagogical objects to aid the reader in understanding the example embodiments and the concepts contributed by the inventor to furthering the art, and are to be construed as being without limitation to such specifically-recited examples and conditions.

What is claimed is:

1. A non-transitory computer-readable medium storing a program configured to cause a processor to generate a user interface on a display device associated with the processor, the user interface comprising:
   a grid including rows and columns;
   a viewport that displays only a portion of the grid;
   a plurality of cells each having a specific position in one of the rows and one of the columns of the grid, a first one of the cells being related to a second one of the cells that is positioned in a different one of the rows and a different one of the columns of the grid from the first cell, the viewport being configured to display, upon selection of the first or second cell, a visual representation of the relationship in the viewport between the first cell and the second cell; and
   a related-cells indicator displayed in the first cell, the related-cells indicator configured to display a number representing the number of other cell(s), including the second cell, to which the first cell is related.

2. The non-transitory computer-readable medium as recited in claim 1, wherein the viewport is configured to display the visual representation of the relationship in a completely visible fashion even where one of the first cell or the second cell is not visible in the viewport at the time of the selection of the other one of the first cell or the second cell.

3. The non-transitory computer-readable medium as recited in claim 1, wherein the viewport is configured to display the visual representation of the relationship using a pop-up window that overlays one or more of the cells of the grid displayed in the viewport and that lists the relationship between the first cell and the second cell.

4. A non-transitory computer-readable medium storing a program configured to cause a processor to generate a user interface on a display device associated with the processor, the user interface comprising:
   a grid including rows and columns;
   a viewport that displays only a portion of the grid;
   a plurality of cells each having a specific position in one of the rows and one of the columns of the grid, a first one of the cells being related to a second one of the cells that is positioned in a different one of the rows and a different one of the columns of the grid from the first cell such that the first cell and the second cell are not capable of being displayed in the viewport at the same time, the viewport being configured to display, upon selection of the first cell displayed in the viewport, a completely visible visual representation in the viewport of the relationship between the first cell and the second cell; and
   a related-cells indicator displayed in the first cell, the related-cells indicator configured to display a number representing the number of other cell(s), including the second cell, to which the first cell is related.

5. The non-transitory computer-readable medium as recited in claim 4, wherein:
   the grid is configured to display the visual representation of the relationship using a line connecting the first cell to the second cell; and
   an aspect of the relationship is represented by the weight of the line.

6. The non-transitory computer-readable medium as recited in claim 4, wherein the grid is configured to display the visual representation of the relationship using a separate interface object that overlays one or more cells in the grid and that lists the relationship between the first cell and the second cell.

7. The non-transitory computer-readable medium as recited in claim 4, wherein the user interface is configured to allow a user to specify the relationship and one or more aspects of the relationship.

8. The non-transitory computer-readable medium as recited in claim 4, wherein:
the grid is configured to display, upon selection of a third one of the cells, a visual representation of a relationship between the second cell and the third cell and thereby also display a visual representation of an indirect relationship between the first cell and the third cell; and
the relationship between the first and second cells has a different relationship type from the relationship between the second and third cells.

9. The non-transitory computer-readable medium as recited in claim 8, wherein:
the relationship between the first and second cells is a "prerequisite" relationship; and
the relationship between the second and third cells is a "see also" relationship.

10. The non-transitory computer-readable medium as recited in claim 4, wherein the relationship is a semantic relationship in which the meaning of words in first content of the first cell are semantically related to the meaning of words in second content of the second cell.

11. The non-transitory computer-readable medium as recited in claim 4, wherein one or more of the cells of the grid are non-rectangular cells.

12. The non-transitory computer-readable medium as recited in claim 4, wherein the viewport is further configured to reposition a gathered version of the second cell, which includes the second cell or a copy of the second cell, out of its original position in the grid and into the viewport in order to display the visual representation of the relationship between the first cell and the second cell.

13. The non-transitory computer-readable medium as recited in claim 12, wherein the viewport is further configured to modify the gathered version of the second cell in its size, shape, or other visual aspect of its appearance.

14. The non-transitory computer-readable medium as recited in claim 12, wherein the viewport is further configured to overlay the gathered version of the second cell on top of the grid.

15. The non-transitory computer-readable medium as recited in claim 14, wherein the viewport is further configured to gray out or otherwise diminish the grid when the gathered version of the second cell is overlaid on top of the grid.

16. The non-transitory computer-readable medium as recited in claim 4, wherein the relationship between the first cell and the second cell is configured to be defined by a user using a drawing palette included within the user interface that includes predefined relational data objects and drawing tools that the user may assign to cell pairs or groupings of cells.

17. The non-transitory computer-readable medium as recited in claim 4, wherein the relationship between the first cell and the second cell is a node along a relational thread.

18. A non-transitory computer-readable medium storing a program configured to cause a processor to generate a user interface on a display device associated with the processor, the user interface comprising:
a grid including rows and columns;
a plurality of cells each having a specific position in one of the rows and one of the columns of the grid, a first one of the cells being related to a second one of the cells that is positioned in a different one of the rows and a different one of the columns of the grid from the first cell;
a related-cells indicator displayed in the first cell, the related-cells indicator configured to display a number representing the number of other cell(s), including the second cell, to which the first cell is related; and
a viewport that displays only a portion of the grid, the viewport not being capable of displaying the second cell simultaneously with the first cell because the specific position of the second cell in the grid is too far from the specific position of the first cell in the grid to be displayed in the viewport at the same time, the viewport being configured, upon selection of the first cell displayed in the viewport, to reposition a gathered version of the second cell out of its specific position in the grid and into a position within the viewport in order to display a completely visible visual representation of the relationship between the first cell and the gathered version of the second cell.

19. The non-transitory computer-readable medium as recited in claim 18, wherein the viewport is further configured to modify the gathered version of the second cell in its size, shape, or other visual aspect of its appearance.

20. The non-transitory computer-readable medium as recited in claim 18, wherein the viewport is further configured to overlay the gathered version of the second cell on top of the grid.

\* \* \* \* \*